United States Patent [19]

May

[11] Patent Number: 4,933,144
[45] Date of Patent: Jun. 12, 1990

[54] COLORIMETRIC GAS MEASURING DEVICE FOR FLUORINE

[75] Inventor: Wolfgang May, Lübeck, Fed. Rep. of Germany

[73] Assignee: Drägerwerk Aktiengesellschaft, Lübeck, Fed. Rep. of Germany

[21] Appl. No.: 167,132

[22] Filed: Mar. 11, 1988

[30] Foreign Application Priority Data

Mar. 12, 1987 [DE] Fed. Rep. of Germany ....... 3707944

[51] Int. Cl.$^5$ ............................................. G01N 31/22
[52] U.S. Cl. ........................................ 422/60; 422/55; 422/58; 422/86; 422/88; 436/124; 436/167; 436/178; 436/181; 436/902
[58] Field of Search ..................... 422/55, 58, 59, 60, 422/83, 86, 87, 88; 436/79, 101, 124, 167, 178, 181, 902

[56] References Cited

U.S. PATENT DOCUMENTS

| | | | |
|---|---|---|---|
| 4,052,162 | 10/1977 | Clarke | 422/81 |
| 4,230,457 | 10/1980 | Leichnitz | 422/86 X |
| 4,259,287 | 3/1981 | Leichnitz | 422/59 |

FOREIGN PATENT DOCUMENTS

| | | | |
|---|---|---|---|
| 1000170 | 1/1957 | Fed. Rep. of Germany . | |
| 2155178 | 9/1985 | United Kingdom | 422/86 |
| 2170599 | 8/1986 | United Kingdom | 422/86 |

OTHER PUBLICATIONS

Nebergall et al., *College Chemistry*, D. C. Heath and Company, 1976, p. 501–502.

*Primary Examiner*—Robert J. Warden
*Assistant Examiner*—Jill Johnston
*Attorney, Agent, or Firm*—Walter Ottesen

[57] ABSTRACT

The invention is directed to a gas measuring device having a pretreatment device for converting the gas to be detected into a substance indicatable via a colorimetric indicator. The gas measuring device simplifies the detection of fluorine and includes a pretreatment device which has a chloride compound containing a metal of the first or second main groups of the periodic system and is exposed to the fluorine and has a chlorine indicator.

8 Claims, 2 Drawing Sheets

4,933,144

COLORIMETRIC GAS MEASURING DEVICE FOR FLUORINE

FIELD OF THE INVENTION

The invention relates to a gas measuring device having a preconditioning arrangement for converting the gas to be detected into a substance indicatable by means of a colorimetric indicator.

BACKGROUND OF THE INVENTION

Such gas measuring devices are known in various embodiments such as in the form of a detecting tube in which a forward layer splits up the gas to be detected into such components which lead to a change in color in the indicating rearward layer. U.S. Pat. No. 4,259,287 discloses a detecting tube wherein such a forward layer is made of a carrier material impregnated with ammonium chloride and a rearward indicating layer is made of a carrier material impregnated with an acid and bromphenol blue.

Other gas measuring devices such as disclosed in U.S. Pat. No. 4,052,162 have a colorimetric indicator tape which is sensitive for a specific type of gas. In order to be able to measure also other gaseous harmful substances with the same indicator tape, the tape is exposed to gas by means of a pretreatment tube wherein the gas component to be detected is converted into indicatable substances. Accordingly, to detect vinyl chloride, the known gas measuring device includes a pretreatment tube wherein the vinyl chloride is oxidized and chlorine is released which can be indicated by the chlorine-sensitive indicator tape.

In addition, detector tubes are known which can be utilized to specifically detect chlorine or bromine and whose reagent comprises ortho-tolidine. In this connection, reference may be had to the German publication "Prüfröhrchen-Taschenbuch", Drägerwerk AG, Lübeck, May, 1985, page 49. A further known testing tube for liquid hydrofluoric acid or volatile fluorides contains as a reagent iron rhodanide with an additive of hydrochloric acid as disclosed in German Patent No. 1,000,170.

None of the known gas detecting devices can detect free fluorine although the limit values of the workplace concentration are set.

SUMMARY OF THE INVENTION

It is an object of the invention to provide a gas measuring device of the type referred to above by means of which fluorine can be detected in a simple manner. According to a feature of the gas detecting device of the invention, a pretreatment arrangement exposed to the fluorine has a chloride compound containing a metal of the first or second main group of the periodic system and a chloride indicator.

The invention affords the advantage that now fluorine is detectable with the chlorine indicator. The chlorine bound in the metal chloride is formed into a fluoride with chlorine being released so that the free chlorine can enter into a color reaction with a chloride indicator.

For use in tape devices, the pretreatment arrangement is advantageously provided as a forward tube mounted ahead of the indicator tape. In this way, also fluorine is detectable by means of tape devices.

In a specially configured embodiment as a fluorine detecting tube, the pretreatment arrangement can be configured as a front layer within a detecting tube containing the indicator as a detecting layer.

For a diffusion detecting tube, it is preferable to configure the pretreatment arrangement as a conversion layer disposed downstream of the indicator layer in the diffusion direction behind which the tube is closed off. The fluorine diffuses through the indicator layer to the conversion layer and the chlorine released there diffuses then in the opposite direction to the indicator layer so as to bring about an indication.

For the specific detection of fluorine, the chloride compound preferably comprises magnesium chloride, which has a high yield of released chlorine and the chlorine indicator preferably comprises o-tolidine.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
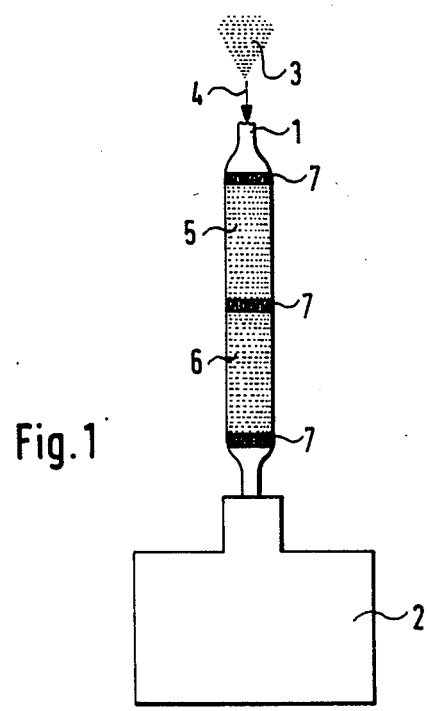
FIG. 1 is a schematic showing a detecting tube connected to a pump apparatus.

FIG. 1 shows a detecting tube 1 open at both ends and connected to a pumping apparatus 2. An air sample 3, which contains free fluorine to be detected, is drawn through a first pretreatment device 5 configured as a front layer and thereafter is drawn through an indicator layer 6. The front layer 5 and the indicator layer 6 are clamped into position with respect to each other and at the open constricted ends of the detecting tube 1 by means of porous holding elements 7.

To detect fluorine in the air sample 3, the front layer 5 comprises a granular filling impregnated with magnesium chloride and the indicator 6 comprises a granular silica gel carrier impregnated with o-tolidine.

Figure 2:
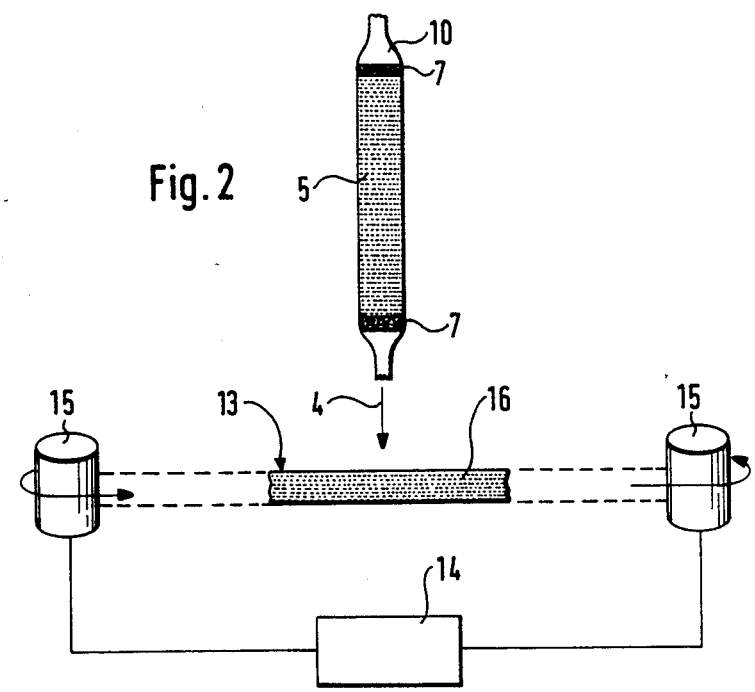
FIG. 2 is a schematic showing a forward tube mounted on a tape device.

In FIG. 2, a granular front layer 5 in the form of a pretreatment device is enclosed between two porous holding elements 7 in a forward tube 10. A pumping or displacing device (not shown) moves the air sample with the fluorine to be detected through the forward tube 10 where the secondary halogen chlorine leaving the forward tube 10 is displaced in the direction of flow arrow 4 toward the indicator tape 13 of a schematically represented colorimetric tape detecting device 14. The tape 13 is windable about the rollers 15 and is provided with an indicator layer 16 made of o-tolidine.

Figure 3:
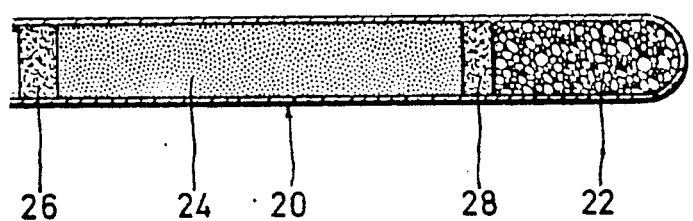
FIG. 3 is a side elevation view of the gas measuring device according to another embodiment of the invention wherein an indicator layer and a conversion layer are arranged to define a diffusion testing tube.

Referring to FIG. 3 and for a diffusion detecting tube 20, it is preferable to configure the pretreatment arrangement as a conversion layer 22 disposed downstream of the indicator layer 24 in the diffusion direction. The tube is closed off directly behind the conversion layer 22. The fluorine diffuses through the indicator layer 24 to the conversion layer 22 which contains a chloride compound which reacts with the fluorine to release chlorine. The chlorine released in this manner diffuses then in the opposite direction to the indicator layer 24 so as to bring about an indication. The indicator layer 24 contains a substance for entering into a color reaction with the chlorine as the latter migrates from the conversion layer 22 into said indicating layer 24.

Porous retaining elements 26 and 28 retain the layers 24 and 22 in position.

For the specific detection of fluorine, the chloride compound preferably comprises magnesium chloride, which has a high yield of released chlorine and the chlorine indicator preferably comprises o-tolidine.

It is understood that the foregoing description is that of the preferred embodiments of the invention and that various changes and modifications may be made thereto without departing from the spirit and scope of the invention as defined in the appended claims.

What is claimed is:

1. A gas measuring device for detecting fluorine, the device comprising:

a pretreatment arrangement including a carrier containing a chloride compound containing a metal selected from groups Ia or IIa of the periodic system wherein said metal is ionically bonded to chlorine in said chloride compound;

said pretreatment arrangement further including means for guiding a gas sample comprising fluorine to said carrier containing said chloride compound thereby permitting the fluorine to displace the chlorine within said chloride compound to release the chlorine; and, colorimetric indicating means for entering into a color reaction with said chlorine thereby detecting said fluorine.

2. The gas measuring device of claim 1, wherein said pretreatment arrangement comprises:

a forward tube for receiving the gas sample comprising the fluorine to be detected; and, said carrier containing said chloride compound being disposed in said tube so as to permit said fluorine to coact therewith to release said chlorine; and, wherein said colorimetric indicating means includes a colorimetric indicator tape mounted in sequential fluid flow communication with said tube and containing a substance for entering into said color reaction with said chlorine thereby detecting said fluorine.

3. The gas measuring device of claim 1, wherein said pretreatment arrangement comprises:

a test tube defining a longitudinal axis and having an opening at one end thereof for receiving said gas sample; and, front layer means mounted in said tube adjacent said opening and including said carrier containing said chloride compound; and, said colorimetric indicating means being disposed in said tube in sequential fluid flow communication with said front layer means.

4. The gas measuring device of claim 3, wherein said colorimetric indicating means is configured as rear layer means.

5. The gas measuring device of claim 4, wherein said test tube is also open at the other end thereof; and, said colorimetric indicating means further includes pump means disposed at said other end for drawing said gas sample through said test tube.

6. The gas measuring device of claim 1, wherein said pretreatment arrangement comprises: an elongated gas-diffusion testing tube having two ends and being closed at one of said two ends; said testing tube further having means formed at the other one of said two ends for admitting said gas sample into said testing tube; and, a conversion layer disposed in said tube adjacent the closed one of said two ends thereof;

said colorimetric indicating means comprises an indicator layer inert to said fluorine and mounted in said testing tube between said other one of said two ends and said conversion layer for conducting said gas sample to said conversion layer;

said conversion layer containing said carrier containing said chloride compound for reacting with said fluorine to release chlorine from said chloride compound; and, said indicating layer containing a substance for entering into said color reaction with said chlorine as said chlorine diffuses from said conversion layer into said indicating layer.

7. The gas measuring device of claim 6, wherein said chloride compound is magnesium chloride and said substance is o-tolidine.

8. The gas measuring device of claim 1, wherein said chloride compound is magnesium chloride and said colorimetric indicating means comprises o-tolidine.

* * * * *